US010335214B2

(12) United States Patent
Appenzeller et al.

(10) Patent No.: US 10,335,214 B2
(45) Date of Patent: Jul. 2, 2019

(54) MULTIPLEXED SCREWS

(75) Inventors: Andreas Appenzeller, Biel (CH); Tom Overes, Langendorf (CH); Robert Frigg, Bettlach (CH); Nicolas Bouduban, Bruegg (CH); Silas Zurschmiede, Grenchen (CH); Simon Stucki, Thun (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 12/766,452

(22) Filed: Apr. 23, 2010

(65) Prior Publication Data
US 2010/0274296 A1    Oct. 28, 2010

Related U.S. Application Data

(60) Provisional application No. 61/172,451, filed on Apr. 24, 2009.

(51) Int. Cl.
*A61B 17/86* (2006.01)
*A61B 17/74* (2006.01)
*A61B 17/80* (2006.01)

(52) U.S. Cl.
CPC ........ *A61B 17/8605* (2013.01); *A61B 17/744* (2013.01); *A61B 17/746* (2013.01); *A61B 17/8057* (2013.01)

(58) Field of Classification Search
USPC .......... 606/305, 280, 70, 283, 284, 319; 623/19.11, 21.11, 21.12, 22.36, 22.37, 623/22.38; 411/457
See application file for complete search history.

(56) References Cited

U.S. PATENT DOCUMENTS

| 3,641,590 | A | * | 2/1972 | Michele | 623/22.37 |
| 4,211,080 | A | | 7/1980 | White | |
| 4,727,700 | A | * | 3/1988 | Eberle | 52/417 |
| 5,032,132 | A | * | 7/1991 | Matsen et al. | 623/19.11 |
| 5,578,034 | A | | 11/1996 | Estes | |
| 6,030,389 | A | * | 2/2000 | Wagner | A61B 17/7059 606/246 |
| 6,890,333 | B2 | | 5/2005 | Von Hoffmann et al. | |
| 6,896,703 | B2 | * | 5/2005 | Barbieri et al. | 623/22.3 |
| 7,001,388 | B2 | | 2/2006 | Orbay et al. | |
| 7,241,314 | B1 | * | 7/2007 | Winslow | A61F 2/40 623/19.13 |
| 2004/0093090 | A1 | | 5/2004 | Barbieri et al. | |
| 2004/0127901 | A1 | * | 7/2004 | Huebner et al. | 606/69 |

(Continued)

FOREIGN PATENT DOCUMENTS

DE    2851155    6/1979
EP    1402833    3/2004

(Continued)

*Primary Examiner* — Zade Coley
(74) *Attorney, Agent, or Firm* — Fay Kaplun & Marcin, LLP

(57) ABSTRACT

A bone fixation element comprises a shaft extending substantially along a longitudinal axis of the fixation element in combination with a head including a plurality of fixation element openings distributed about a perimeter thereof. Each of the fixation element openings extends through the head from a proximal surface thereof to a distal surface of the head. Each of the fixation element openings extends through the head along an opening axis.

30 Claims, 15 Drawing Sheets

(56) References Cited

U.S. PATENT DOCUMENTS

| | | | |
|---|---|---|---|
| 2005/0090826 A1* | 4/2005 | Keller | A61B 17/7059 606/70 |
| 2005/0256583 A1* | 11/2005 | Bouttens | A61F 2/4081 623/19.13 |
| 2006/0149249 A1 | 7/2006 | Mathoulin et al. | |
| 2007/0142922 A1* | 6/2007 | Lewis et al. | 623/22.36 |

FOREIGN PATENT DOCUMENTS

| | | |
|---|---|---|
| FR | 2704747 | 11/1994 |
| FR | 2851155 | 8/2004 |
| JP | H1156870 | 3/1999 |
| JP | 2003/518408 | 6/2003 |
| JP | 2008/206789 | 9/2008 |
| WO | 2004/008980 | 1/2004 |
| WO | 2005/102192 | 11/2005 |
| WO | 2005/102195 | 11/2005 |
| WO | 2007/056516 | 5/2007 |

* cited by examiner

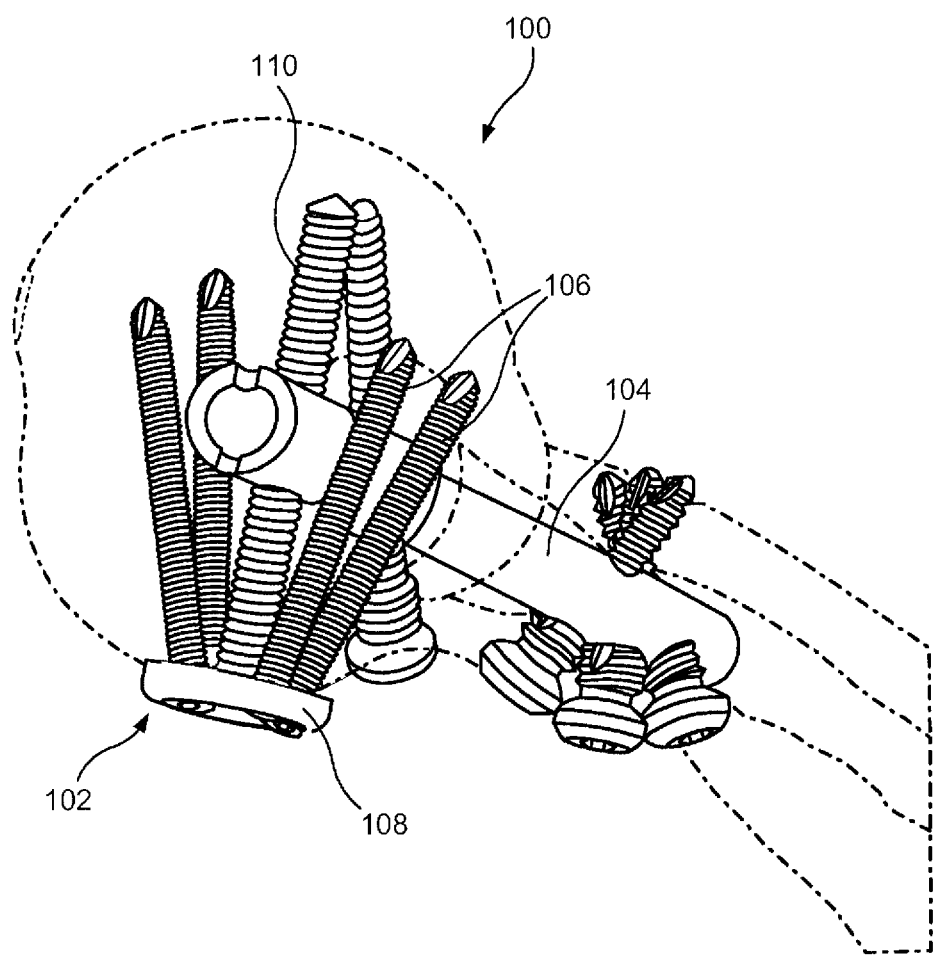
F I G. 14

MULTIPLEXED SCREWS

PRIORITY CLAIM

The present application claims priority to U.S. Provisional Application Ser. No. 61/172,451 entitled "Multiplexed Screws" filed on Apr. 24, 2009; the entire disclosure of which is incorporated herein by reference.

FIELD OF THE INVENTION

The present invention relates to devices for treating fractures and, in particular, relates to an osteosynthetic implant such as a screw including a plurality of openings, which allow a variety of bone fixation elements to fix a fracture within a limited amount of space.

BACKGROUND

Fractures of bones may be fixed using devices such as plates, nails and screws. A variety of different bone fixation elements are currently available such as, for example, locking head screws, variable angle screws, pins and blades. Plates and nails, however, are generally limited to engaging with a specific types of bone fixation elements. Additionally, in certain situations, only a small amount of space is available to fix and reposition bone fragments limiting the techniques suitable for fixing such fractures.

SUMMARY OF THE INVENTION

The present invention is directed to a bone fixation element, comprises a shaft extending substantially along a longitudinal axis of the fixation element in combination with a head including a plurality of fixation element openings distributed about a perimeter thereof, each of the fixation element openings extending through the head from a proximal surface thereof to a distal surface of the head, each of the fixation element openings extending through the head along an opening axis.

BRIEF DESCRIPTION OF THE DRAWINGS

FIG. 14 shows another perspective view of the system of FIG. 13;

DETAILED DESCRIPTION

Figure 1:
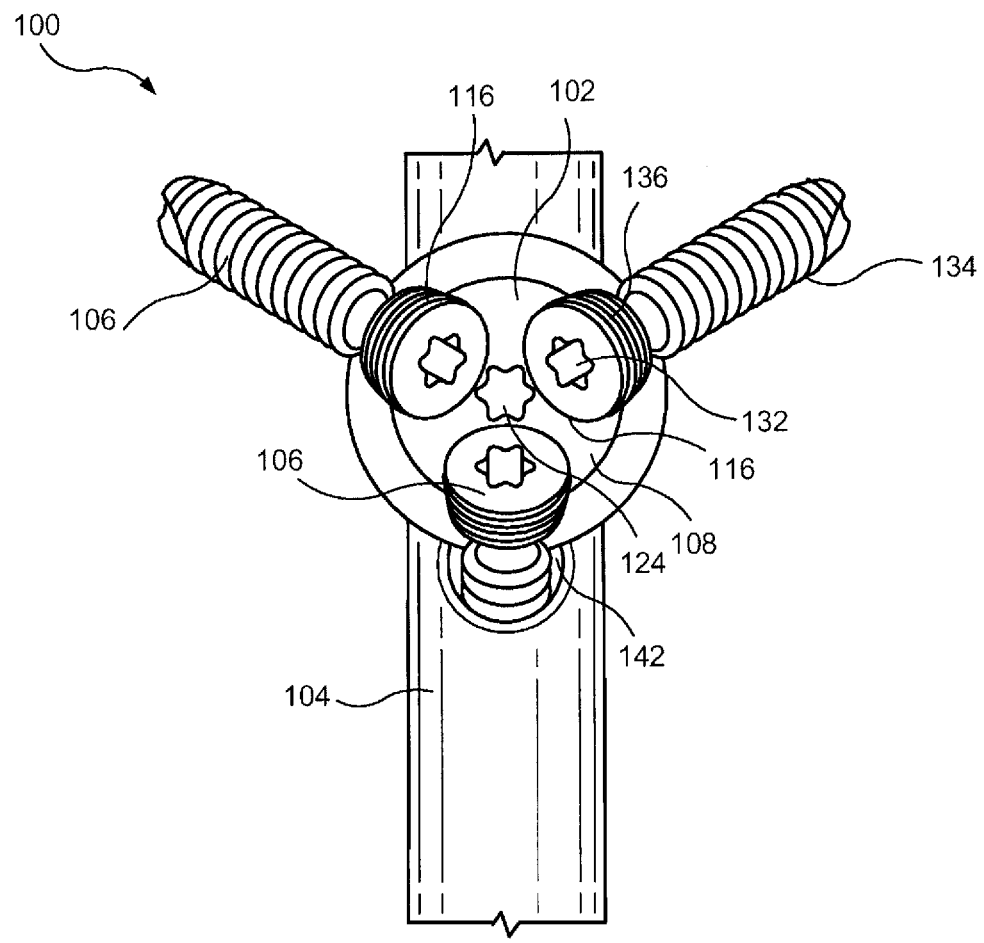
FIG. 1 shows a front view of a system according to a first exemplary embodiment of the present invention.

The present invention may be further understood with reference to the following description and the appended drawings, wherein like elements are referred to with the same reference numerals. The present invention relates to devices for treating fractures and, in particular, relates to an osteosynthetic implant such as a screw. Exemplary embodiments of the present invention provide a multiplexed screw including a plurality of openings, which allow a variety of bone fixation elements to fix a fracture within a limited amount of space. It should be noted that the terms of proximal and distal, used herein, are not used to reference any particular direction, but are used to describe a direction toward (proximal) and away (distal) from a surgeon or other user of the device.

As shown in FIGS. 1-11, a system 100 comprises a multiplexed screw 102 insertable into an implant 104 to allow a plurality of bone fixation elements 106 to be inserted therethrough to fix a fracture of the bone. The implant 104 may be any osteosynthetic implant such as, for example, a bone plate, a nail, etc. It will be understood by those of skill in the art, however, that the implant 104 may not be required as the multiplexed screw 102 may also be inserted directly into the bone. It will also be understood by those of skill in the art that the multiplexed screw 102 may be used to fix a variety of different types of fractures, especially those in which the space which may be occupied by the screw is limited.

Figure 3:
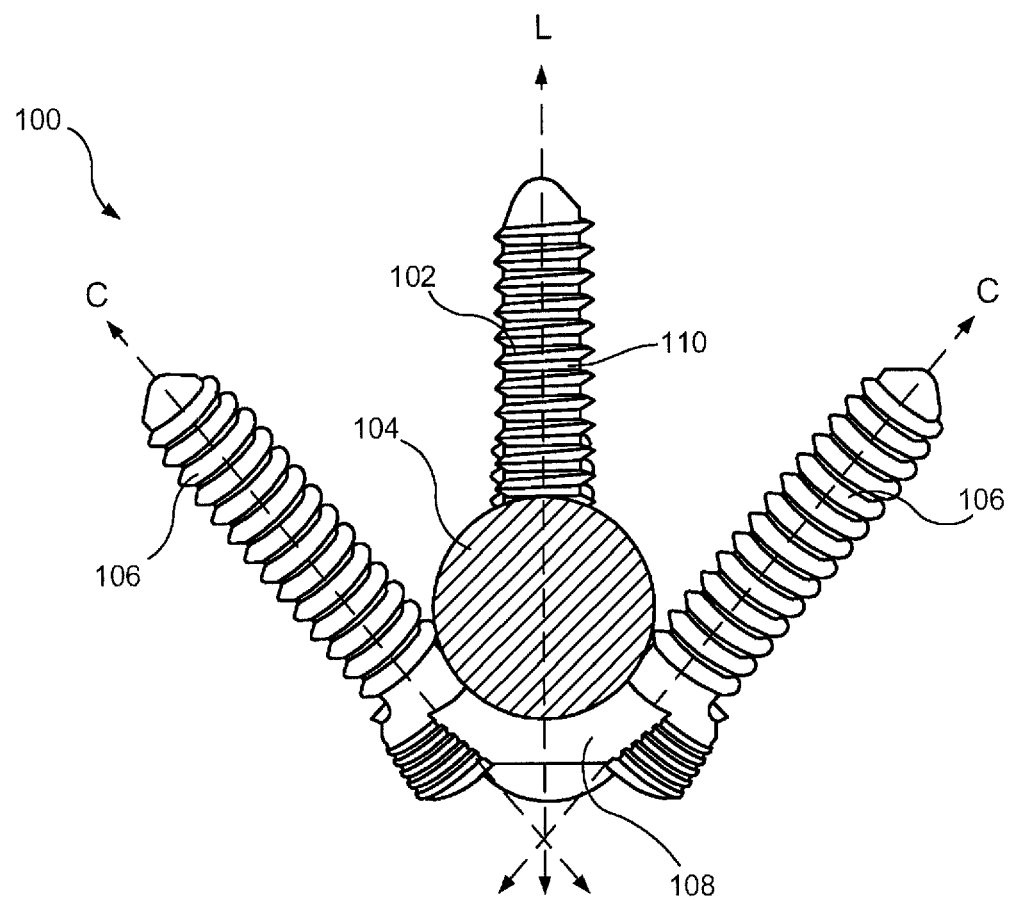
FIG. 3 shows a top view of the system of FIG. 1.
Figure 5:
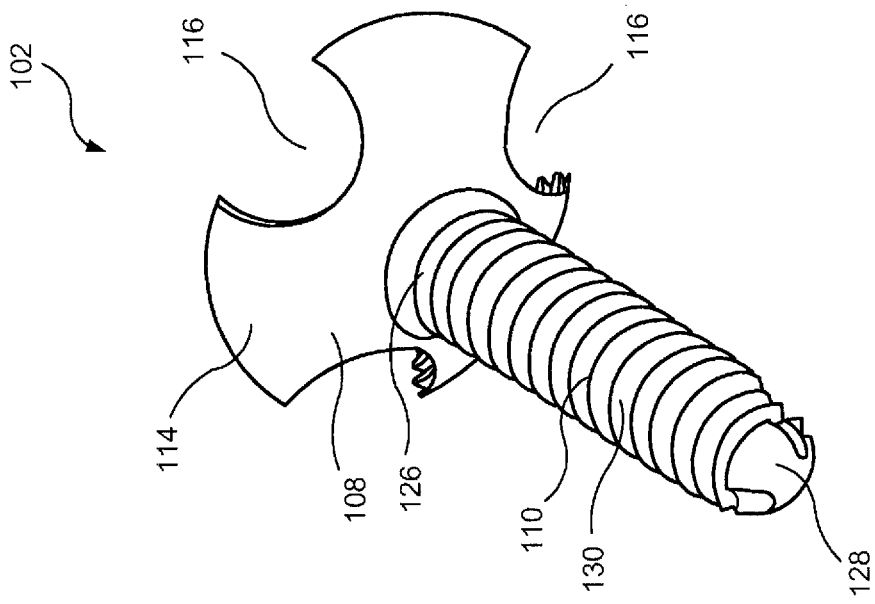
FIG. 5 shows a second perspective view of the multiplexed screw of FIG. 4.
Figure 4:
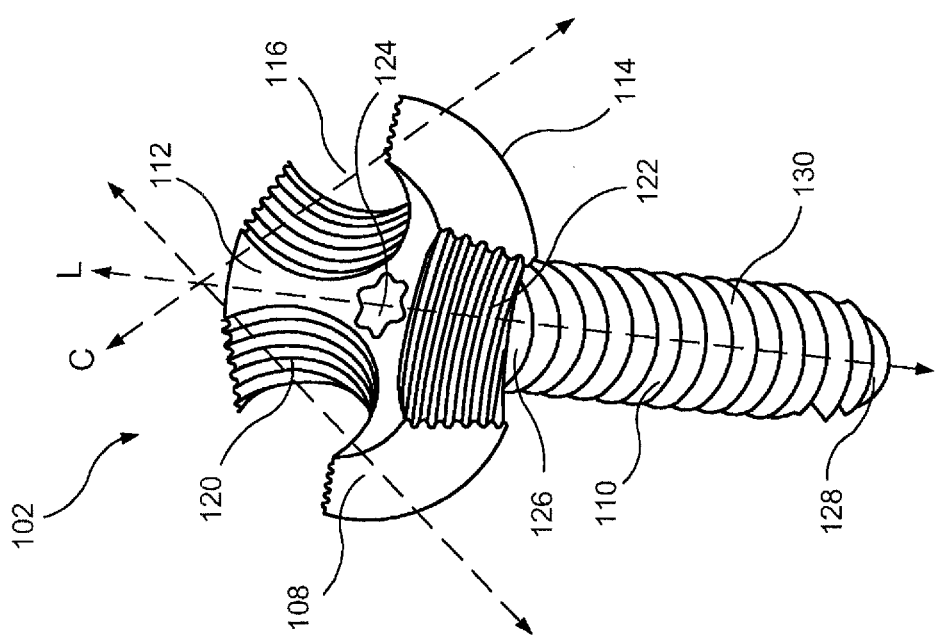
FIG. 4 shows a first perspective view of a multiplexed screw according to the system of FIG. 1.
Figure 6:
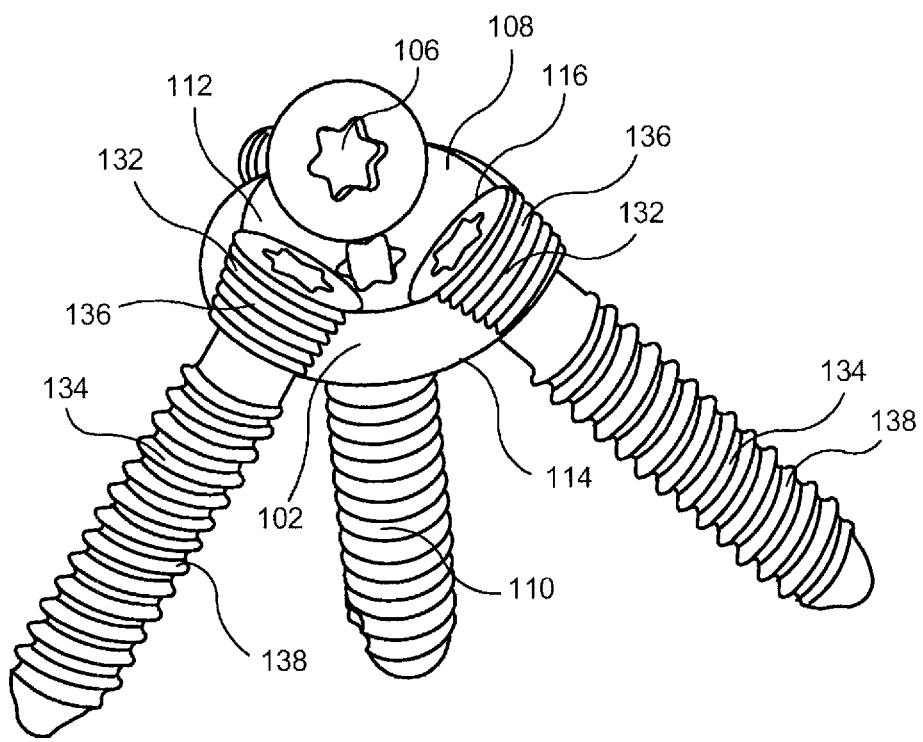
FIG. 6 shows a first perspective view of the multiplexed screw and a plurality of bone fixation elements of the system of FIG. 1.
Figure 7:
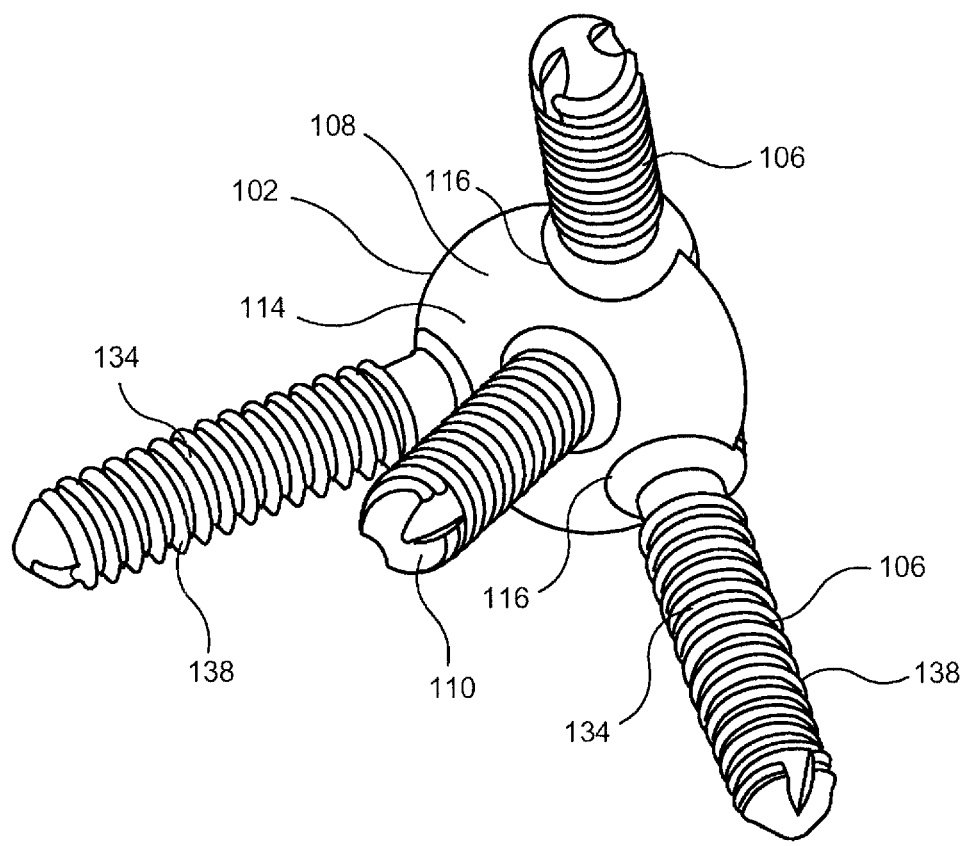
FIG. 7 shows a second perspective view of the multiplexed screw and the plurality of bone fixation elements of FIG. 6.
Figure 8:
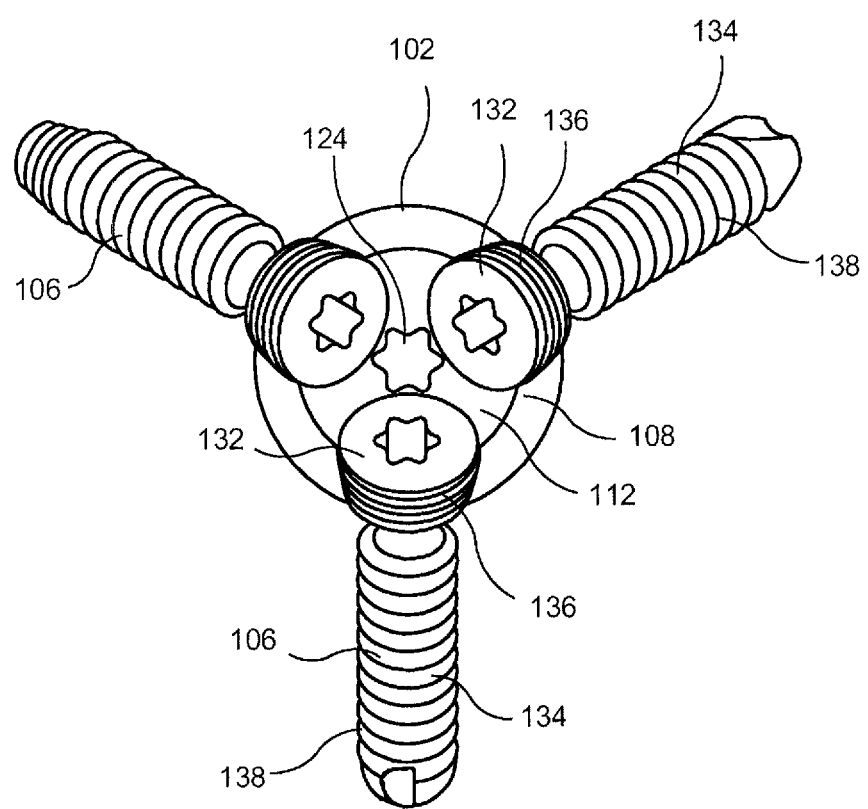
FIG. 8 shows a top view of the multiplexed screw and the plurality of bone fixation elements of FIG. 6.
Figure 9:
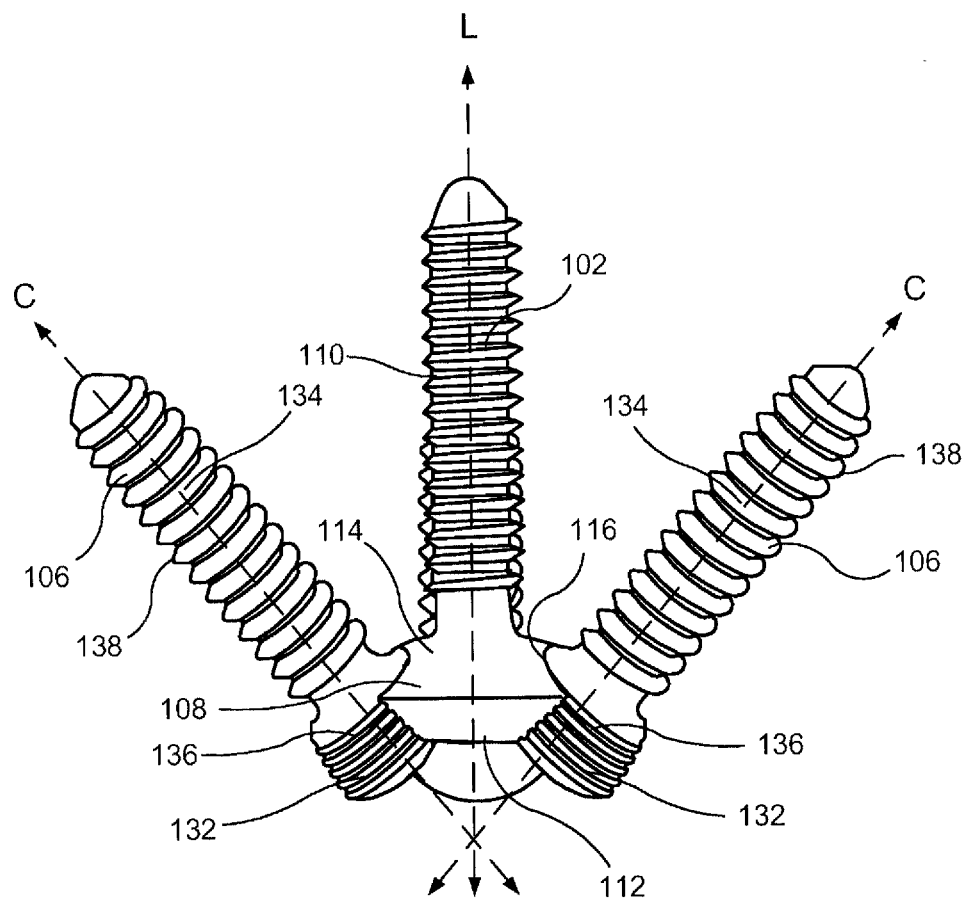
FIG. 9 shows a side view of the multiplexed screw and the plurality of bone fixation elements of FIG. 6.

As shown in FIGS. 3-5, the multiplexed screw 102 includes a head 108 and a body portion 110 extending distally therefrom. In a preferred embodiment, the head 108 and the body portion 110 are integrally formed. The head 108 includes a proximal surface 112 which, when inserted into a bone in an operative position, faces away from the bone and a distal surface 114 which, in the operative position, faces the bone. The head 108 also includes a plurality of openings 116 distributed about a perimeter of the head 108 each sized and shaped to accommodate a bone fixation element 106 therein.

Figure 10:
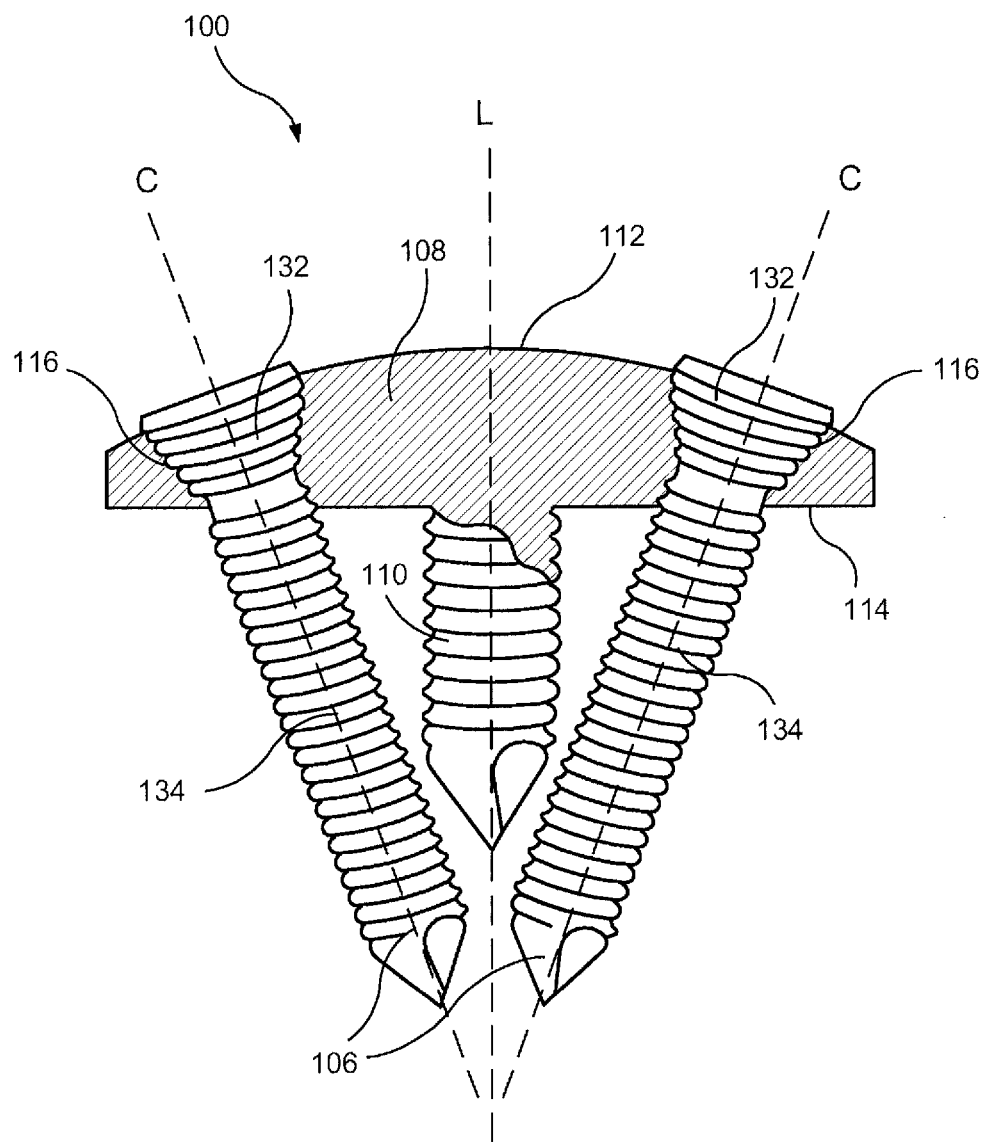
FIG. 10 shows a cross-sectional side view of an alternate embodiment of the multiplexed screw and the plurality of bone fixation elements of FIG. 6.
Figure 11:
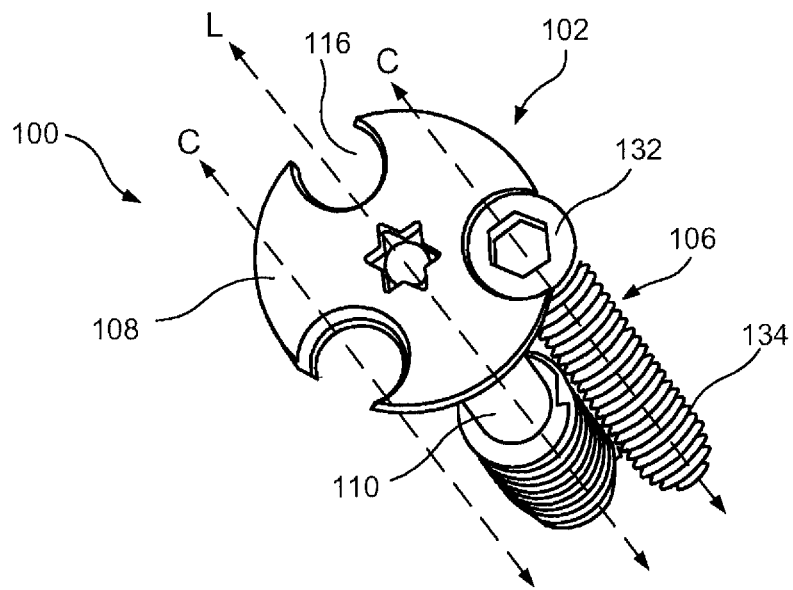
FIG. 11 shows a perspective view of another alternate embodiment of the multiplexed screw of the and the plurality of bone fixation elements of FIG. 6.

In a first exemplary embodiment, as shown in FIGS. 1-9, the proximal surface 112 may be substantially concave while the distal surface 114 may be substantially convex. Each of the openings 116 extends through the head 108, from the proximal surface 112 to the distal surface 114, substantially perpendicularly to the proximal surface 112 such that the openings 116 are oriented so that a central axis C of each of the openings 116 intersects a longitudinal axis L of the multiplexed screw 102 at a point proximal of the proximal surface 112, at an angle up to 70° relative to the longitudinal axis L. In an alternate embodiment, as shown in FIG. 10, the proximal surface 112 may be substantially convex and/or the distal surface 114 may be substantially concave such that a central axis C of each of the openings 116 intersects the longitudinal axis L at a point distal of the distal surface 114 at an angle up to −45° relative to the longitudinal axis L. In another alternative embodiment, as shown in FIG. 11, the central axis C of the openings 116 does not interest with the longitudinal axis L at either a point proximal of the proximal surface 112 or distal of the distal surface 114. Rather, the central axes C may also extend through the head 108 such that the central axes C are substantially parallel to the longitudinal axis L. In addition, the proximal and/or distal surfaces 112, 114 may be substantially planar.

Figure 12:
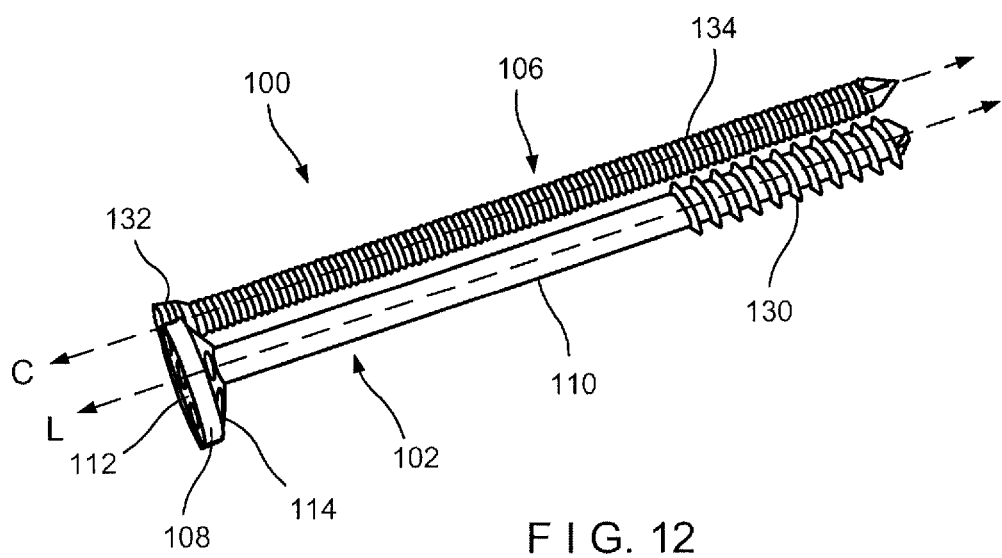
FIG. 12 shows a side view the multiplexed screw and the plurality of bone fixation elements of FIG. 6.
Figure 13:
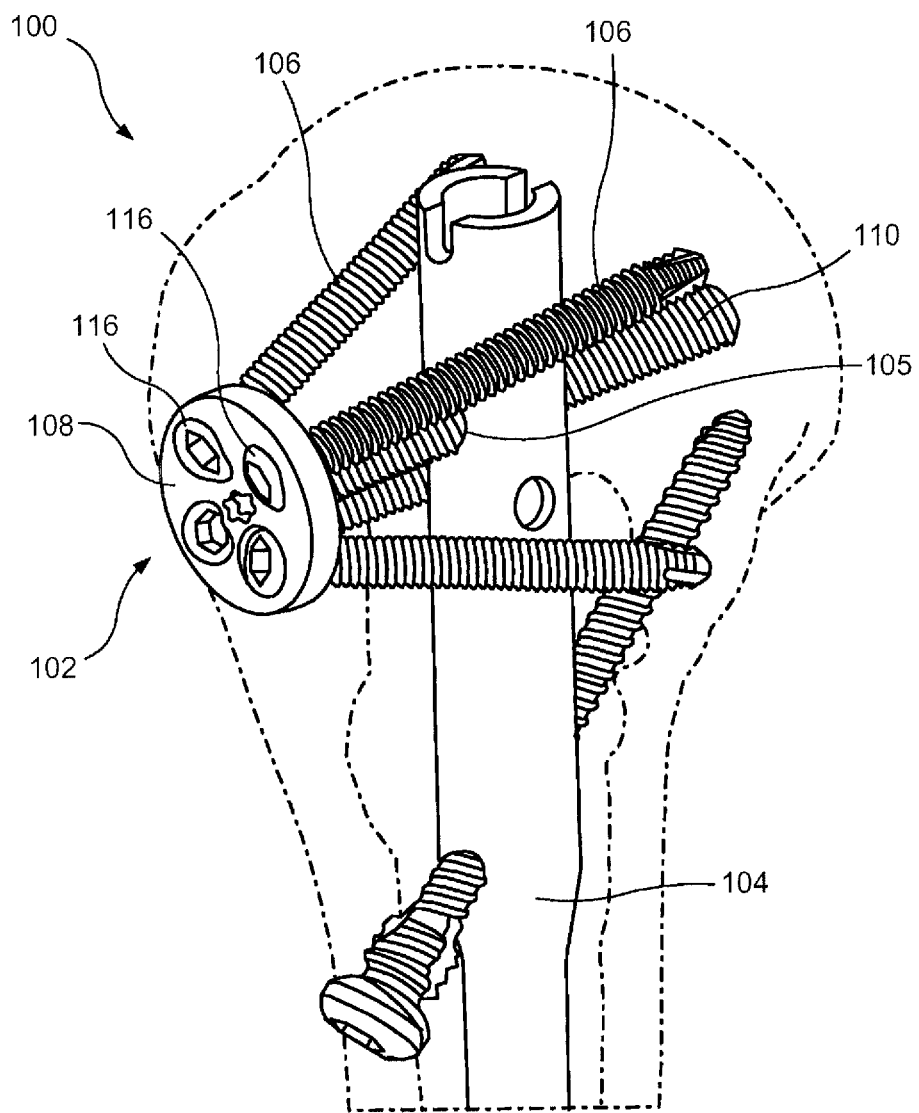
FIG. 13 shows a perspective view of an exemplary surgical system according to the present invention.

As would be understood by those skilled in the art, the angles of intersection between the central axes C and the longitudinal axis L may be equal to one another or different depending on the requirements of a particular application. Specifically, these angles are selected so that a plurality of bone fixation elements inserted into the bone via the screw 102 are spread away from the longitudinal axis L (and the body portion 110) by a desired amount thereby increasing an area of bone fixed by the bone fixation elements. To reduce the size of the head 108, the openings 116 may be only partially enclosed by the head 108—i.e., a proximal portion of each of the openings 116 may be left open. Thus, each of the openings may be enclosed from between more than 180° to 360°, where the opening 116 is fully enclosed, as shown in FIGS. 12-14. In a preferred embodiment, the openings 116 may be enclosed between approximately 240° and 270°.

One or more of the openings 116 may include threading 122 along an inner surface 120 thereof to engage a corresponding threading on a locking head of a bone fixation element 106 to be inserted therethrough. The threading 122 may be formed, for example, along a helical path corresponding to a path of the threading of a locking head of a bone fixation element to be inserted therethrough. Although, in a preferred embodiment, the head 118 may include three openings 116, it will be understood by those of skill in the art, that the head 108 may include any number of openings 116.

In a preferred embodiment, the head 108 may be substantially circular such that the head 108 may allow the plurality of bone fixation elements 106 to be inserted therethrough in the smallest amount of space. In a preferred embodiment, the head 108 may have a diameter of less than 40 mm. However, it will be understood by those of skill in the art that a size of the head 108 may vary depending on a number of factors such as, for example, a number of openings 116, a size of the bone fixation elements 106 accommodated by the openings 116 and an angle of the central axes C relative to the longitudinal axis L. It will also be understood by those of skill in the art that the head 108 may take a variety of shapes and sizes. The head 108 may also include a mating element 124 on the proximal surface 112, sized and shaped to mate with a driving tool. In a preferred embodiment, the mating element 124 may be a hexagonally shaped recess matable with a hexagonally shaped portion of a driving tool. It will be understood by those of skill in the art, however, that the mating element 124 may be any recess or protrusion matable with a driving tool such that the multiplexed screw 102 may be rotated about the longitudinal axis as it is being inserted into the implant 104.

The body portion 110 may extend longitudinally from a proximal end 126 to a distal end 128, the proximal end 126 attached to the distal surface 114 of the head 108. The body portion 110 may include a threading 130 along at least a portion of a length thereof to engage the implant 104. It will be understood by those of skill in the art that the multiplexed screw 102 is insertable through an opening 140 of the implant 104 to fix the implant 104 relative to the bone. The body portion 110 is thus sized and shaped to be insertable through the opening 140 of the implant 104. It will also be understood by those of skill in the art that the multiplexed screw 102 may be formed of a variety of bio-compatible materials such as, for example, steel, titanium and PEEK.

Figure 2:
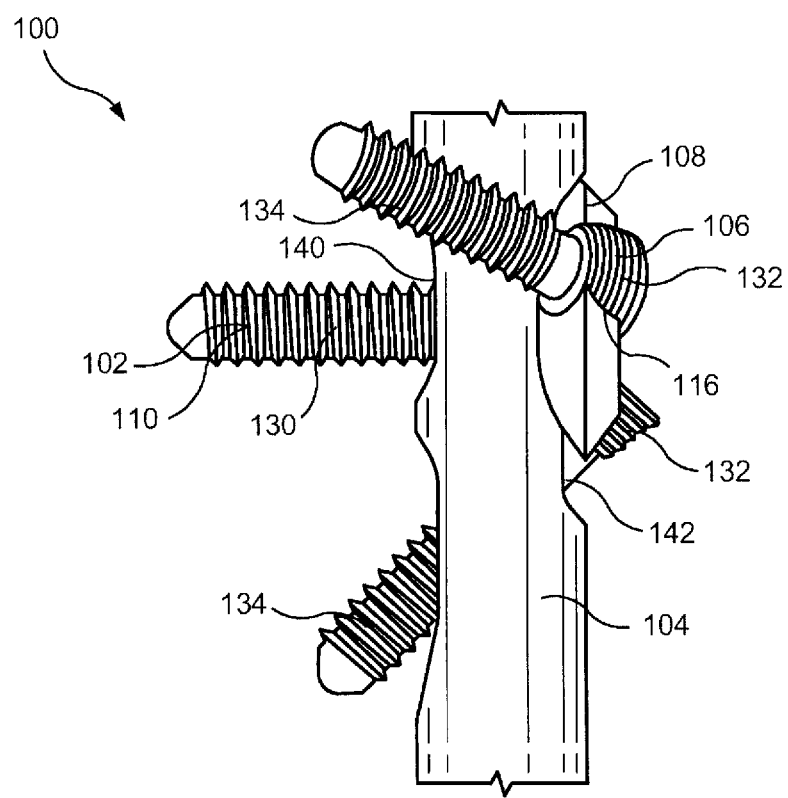
FIG. 2 shows a side view of the system of FIG. 1.

The plurality of bone fixation elements 106 may include any type of bone fixation element such as, for example, a locking head screw. As shown in FIGS. 6-9, each of the plurality of bone fixation elements may include a head 132 and a shaft 134 extending therefrom. The head 132 may include a threading 136 or other engaging mechanism therearound such that the head 132 may engage with the threading 122 of any of a plurality of openings 116. The shaft 134 may also include a threading 138 along at least a portion of a length thereof to engage the bone. Each of the bone fixation elements 106 is insertable along the central axis C of each of the openings 116. Depending on the angle of intersection of the central axis C and the longitudinal axis L, the shaft 134 of the bone fixation element 106 may flare outward relative to the longitudinal axis L as it is inserted further into the bone (i.e., distal of the distal surface 114 of the multiplexed screw 102), as shown in FIGS. 6-9, inward relative to the longitudinal axis L, as shown in FIG. 10, or parallel relative to the longitudinal axis L, as shown in FIGS. 11-12. It will be understood by those of skill in the arty that the plurality of bone fixation elements 106 are able to fix a larger area of bone through a small amount of space than would be fixed by the shaft of a single bone fixation element. It will also be understood by those of skill in the art that each of the bone fixation elements 106 is insertable through one or more of the openings 116 to engage either the bone or another opening 142 of the implant 104, as shown in FIGS. 1-3.

According to an exemplary surgical use of the system 100, as shown in FIGS. 13-14, the screw 102 may be used with an implant 104 such as an intramedullary nail to treat, for example, a femoral neck fracture. The body portion 110 of the screw 102 (shown with the plurality of openings 116 fully enclosed) may be inserted into the bone and through a hole 105 in the intramedullary nail 104 until the head 108 abuts an outer surface of the bone. Bone fixation elements 106 may then be inserted through the openings 116. In the embodiment shown, the bone fixation elements 106 flare outward with respect to the longitudinal axis L of the screw 102 such that the bone fixation elements 106 extend along either side of the intramedullary nail 104 to provide additional fixation and stability. It will be understood by those of skill in the art additional fixation elements may be inserted through other holes of the intramedullary nail 104 to fix the intramedullary nail 104 relative to the bone.

Figure 15:
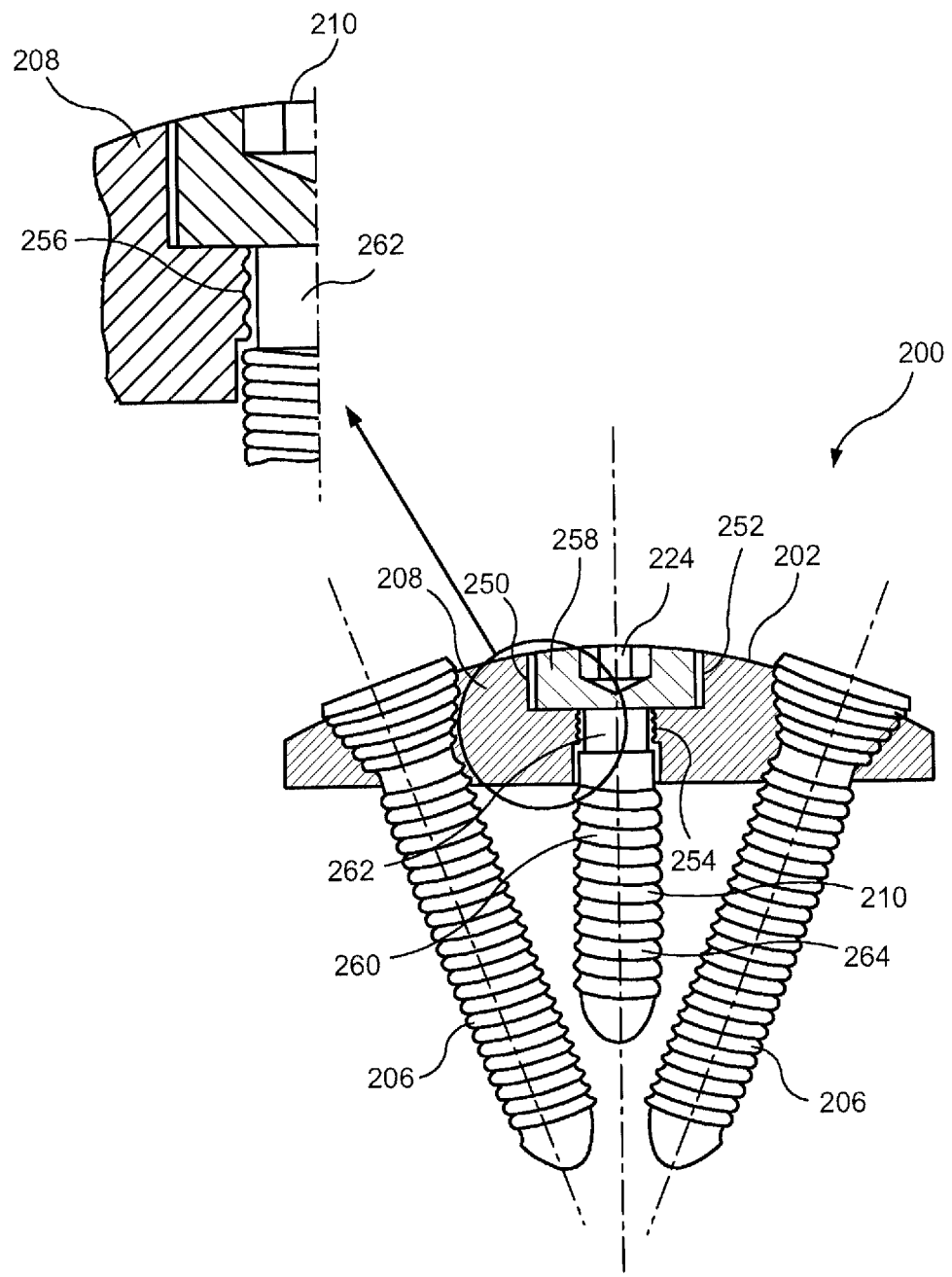
FIG. 15 shows a side view of a system according to a second exemplary embodiment of the present invention.

In a second exemplary embodiment, as shown in FIG. 15, a system 200 comprises a multiplexed screw 202 adapted and configured to receive a plurality of bone fixation elements 206 therethrough. Similarly to the multiplexed screw 102, the multiplexed screw 202 includes a head 208 and a body portion 210. However, the head 208 and the body portion 210 form a two-part assembly such that the head 208 and the body portion 210 are movable relative to one another. Specifically, the head 208 and the body portion 210 in this embodiment are rotatable relative to one another about a longitudinal axis L thereof.

The head 208 may be substantially similar to the head portion 108, including openings 216 similar to the openings 116, but additionally includes a central opening 250 extending therethrough with a first portion 252 of the central opening 250 accommodating a proximal end 258 of a body portion 210 of the screw 202 while a second portion 254 accommodates a reduced diameter part 262 connecting the proximal end 258 to a distal part 260 of the body portion 210. The first portion 252 is greater in diameter than the second portion 254 so that the increased diameter proximal end 258 cannot pass distally therethrough. The second portion 254 includes a threading 256 for engaging a corresponding threading 264 on the distal part 260 as the body portion 210 is installed in the head 208. The proximal end 258 may further include a driving element 224 at a proximal end thereof for engaging a driving tool as would be understood by those skilled in the art. The body portion 210 may be driven distally through the opening 250 via the driving element 224 until the threading of the 264 of the distal part 260 disengages from the threading 256 of the central opening 250 and the second portion 254 receives the reduced diameter portion 262. Thus, a distal end of the threading 256 of the central opening 250 surrounds proximal end of the threading 264 allowing the body portion 210 to rotate within the head 208 and preventing the body portion 210 from being inadvertently removed therefrom.

It will be understood by those of skill in the art that the system 200 may be used in substantially the same manner as described above in regard to the system 100. Specifically, once the body portion 210 has been permanently mounted within the head 208 of the multiplexed screw 202, the multiplexed screw 202 may be driven via the driving element 224 into an opening of an implant and/or a bone. Bone fixation elements 206 may then be inserted along a central axis of each of the openings 216 to fix the bone as desired.

Figure 16:
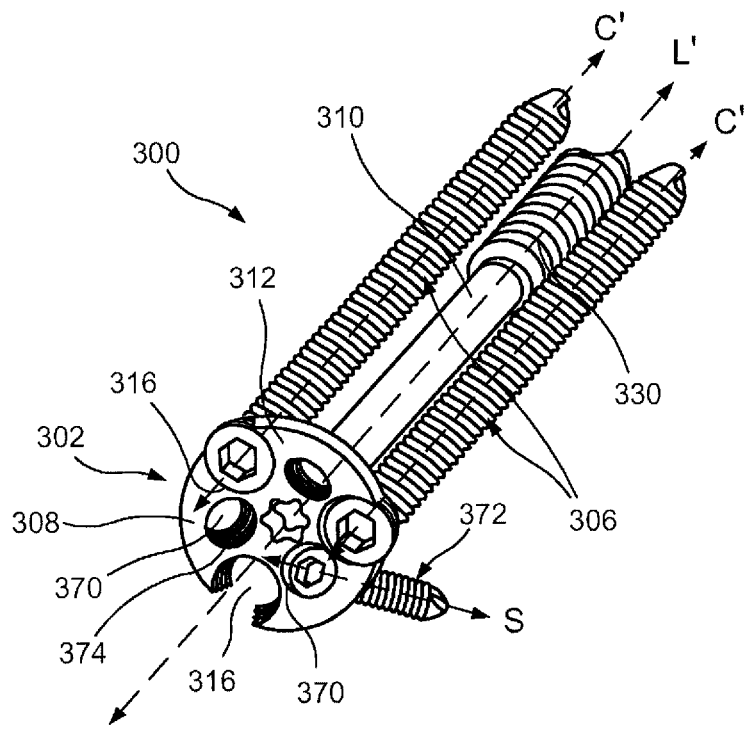
FIG. 16 shows a perspective view of a system according to a third exemplary embodiment of the present invention.
Figure 17:
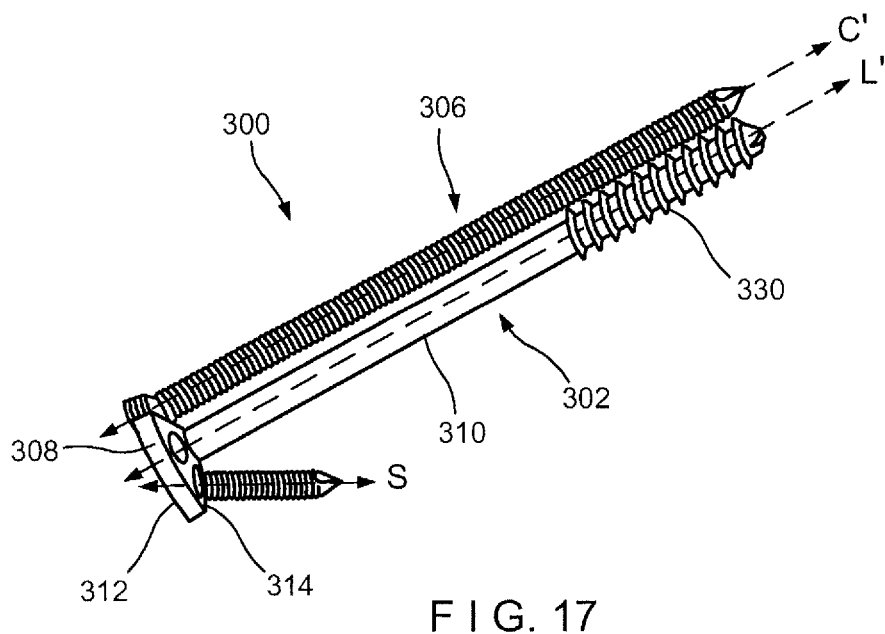
FIG. 17 shows a side view of a system of FIG. 16.
Figure 18:
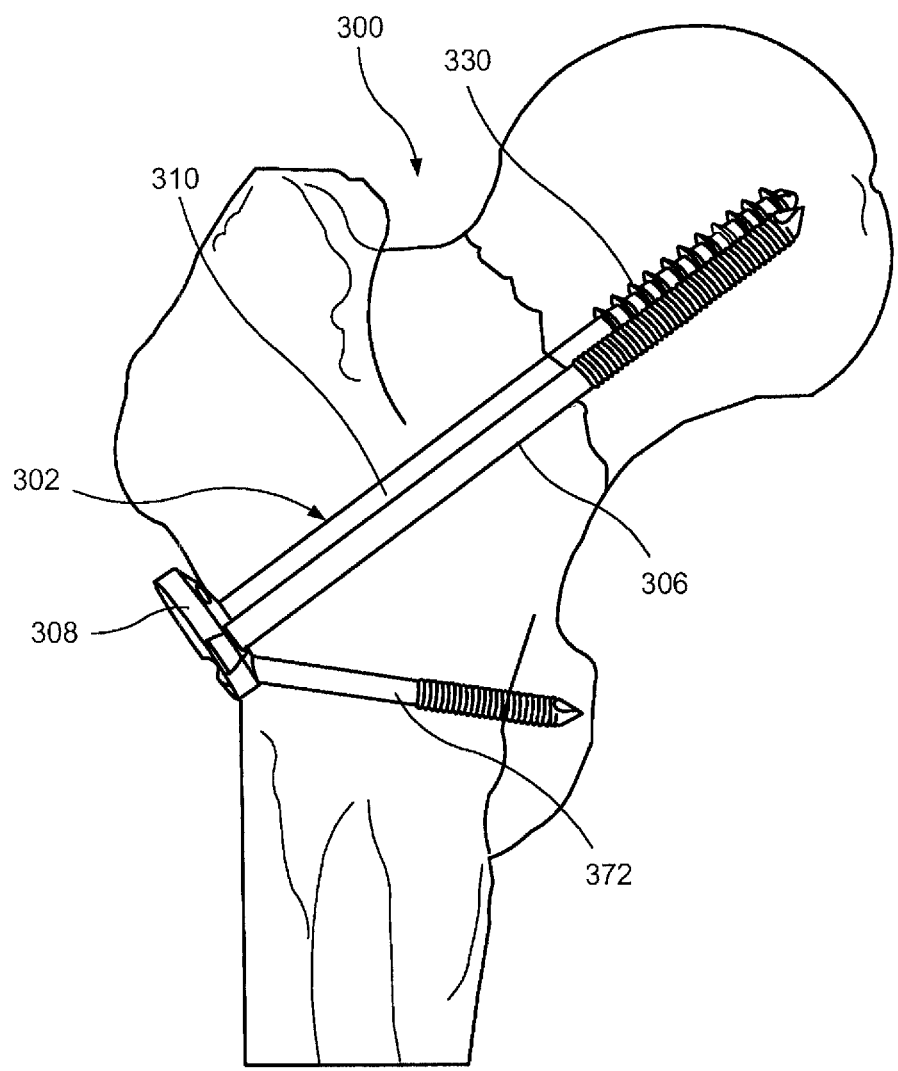
FIG. 18 shows a side of the system of FIG. 16 being used to fix a fracture of a bone.

As shown in FIGS. 16-18, a system 300 according to a third exemplary embodiment is substantially similar to the system 100 described above with a screw 302 substantially similar to the screw 102. The screw 302 has a head 308 and, extending distally therefrom, a body 310 insertable into a target bone 304. The body 310 includes threading 330 extending along at least a portion of a length thereof and the head 308 includes a plurality of a first type of openings 316 extending therethrough from a proximal surface 312 to a distal surface 314 thereof. The openings 316 are substantially similar to the openings 116. The first type of opening 316 is configured to receive a first type of bone fixation element 306, which may be inserted therethrough to provide rotational stability and/or provide additional bending strength. The head 308 additionally includes at least one second type of opening 370 extending therethrough from the proximal surface 312 to the distal surface 314 for receiving a second type of bone screw 372, which locks the screw 302 to the bone. In a preferred embodiment, the screw 302 includes three second type openings 370.

In a preferred embodiment, each of the openings of the first type 316 defines a central axis C' substantially parallel to a longitudinal axis L' of the screw 302 such that the first type of bone fixation elements 306 extend through the openings 316 substantially parallel to the body 310 of the screw 302. It will be understood by those of skill in the art, however, the central axes C' may also intersect with the longitudinal axis L' proximally of the proximal surface 312 or distally of the distal surface 314, as discussed above in regard to the system 100, such that the first type of bone fixation elements 306 flare outward or inward, respectively, relative to the longitudinal axis L'.

Each of the openings 370 of the second type has a central axis S intersecting with the longitudinal axis L' proximally of the proximal surface 312. In a preferred embodiment, the central axis S intersects the longitudinal axis L' at an angle of approximately 30°. It will be understood by those of skill in the art, however, that this angle of intersection may vary depending on the requirements of the particular application. The second type of bone fixation element 370 may be entirely enclosed and include a threading 374 along an inner surface thereof for accommodating a corresponding threading along a head portion (not shown) of the second type of bone fixation element 372. The second type of bone fixation element 372 may be inserted through the second type of opening 370 after the first type of bone fixation element 306 has been inserted through the first type of opening 316, to lock the screw 302 to the bone and prevent the screw 302 from backing out of the bone. It will be understood by those of skill in the art that screw 302 may include additional types of openings extending through the head 308 at varying angles for accommodating different sizes and/or types of bone fixation elements. The head 308 may also include additional openings for accommodating a guide wire. It will also be understood by those of skill in the art that the screw 302 may include more than one second type of opening 370 with the intersections between the central axes S and the longitudinal axis L' being equal to one another or different depending on the requirements of the particular application.

As shown in FIG. 18, the system 300 may be used to fix a fracture in a neck portion of a bone such as, for example, a femur. According to an exemplary surgical technique of the system 300, a k-wire may be inserted into the bone to temporarily align the fractured portions of the bone. An additional k-wire may be placed in the bone to correspond to a desired position of the screw 302. A drill may then be slid over the additional k-wire to drill a hole therethrough. Once the hole has been drilled, the body of the 310 of the screw 302 is inserted through the hole and rotated about the longitudinal axis L' such that the screw 302 is tightened via threading 330 engaging surrounding bone. As the screw 302 is tightened, the fracture is compressed allowing the k-wire (s) providing temporary fixation to be removed.

Drill guides may then be placed in the first type of openings 316 to facilitate the drilling of corresponding holes in the bone. The first type of bone fixation screws 306 are then inserted into the openings 316, providing rotational stability of the screw 302 and/or providing additional support for fixation of the fracture. Once the desired number of bone fixation elements 306 has been inserted through the bone and engaged to the head 308 of the screw 302, a drill guide is inserted through the opening 370 and a corresponding hole is drilled into the bone. A bone fixation element 372 of the second type is then inserted into the bone via the opening 370 to lock the screw 302 to the bone and prevent the screw 302 from backing out of the bone. It will be understood by those of skill in the art that the above-described surgical technique may be similarly used for the system 100. Since the system 100, however, does not include a second type of opening, a second type of bone fixation element is not inserted through any portion thereof.

It will be apparent to those skilled in the art that various modifications may be made in the present invention without departing from the spirit or the scope of the invention. Thus, it is intended that the present invention cover the modifications and variations of this invention provided that they come within the scope of the appended claims and their equivalents.

What is claimed is:

1. A bone fixation element, comprising:
  a shaft extending substantially along a longitudinal axis of the fixation element; and a head extending from and integrally formed with the shaft, the head defining a plurality of fixation element openings distributed about a perimeter thereof, each of the fixation element openings extending through the head from a proximal surface thereof to a distal surface of the head, each of the fixation element openings extending through the head along an opening axis, wherein at least two of the fixation element openings are only partially enclosed by the head, wherein a first one of the openings includes a threading along an inner surface thereof to lockingly engage a corresponding threading on a head of a bone fixation element to be inserted therethrough.

2. The fixation element of claim 1, wherein each of the fixation element openings is angled relative to the longitudinal axis so that points of intersection of the opening axes and the longitudinal axis are proximal of the head.

3. The fixation element of claim 2, wherein the proximal surface is substantially concave and the distal surface is substantially convex such that the opening axis of each of the openings is substantially perpendicular to the proximal surface.

4. The fixation element of claim 2, wherein an angle of intersection between a first one of the opening axes and the longitudinal axis is less than 70°.

5. The fixation element of claim 1, wherein each of the fixation element openings is angled relative to the longitudinal axis so that points of intersection of the opening axes and the longitudinal axis are distal of the head.

6. The fixation element of claim 5, wherein the proximal surface is substantially convex and such that the opening axis of each of the openings is substantially perpendicular to the proximal surface.

7. The fixation element of claim 5, wherein an angle of intersection between a first one of the opening axes and the longitudinal axis is smaller than −45°.

8. The fixation element of claim 1, wherein at least two of the openings are partially enclosed by the head.

9. The fixation element of claim 8, wherein the at least two openings are surrounded by a surface formed by the head over an angle of between 240° and 270°.

10. The fixation element of claim 1, wherein an angle of a first opening axis is equal to an angle of a second opening axis.

11. The fixation element of claim 1, wherein the opening axis of each of the fixation element openings is substantially parallel to the longitudinal axis of the fixation element.

12. The fixation element of claim 1, wherein the head further includes a locking hole extending therethrough from the proximal surface to the distal surface along a locking axis, the locking hole being adapted and configured for receiving a locking element.

13. The fixation element of claim 12, wherein the locking axis intersects the longitudinal axis at a point proximal of the proximal surface of the head.

14. The fixation element of claim 13, wherein an angle of intersection of the locking axis and the longitudinal axis is approximately 30°.

15. The fixation element of claim 1, wherein the shaft is threaded to threadably engage the bone.

16. The bone fixation element of claim 1, wherein the bone fixation element is a bone screw.

17. The bone fixation element of claim 1, wherein the circumference of the at least two fixation element openings is enclosed more than 180 degrees.

18. The bone fixation element of claim 17, wherein the circumference of the at least two fixation element openings is enclosed between 240 and 270 degrees.

19. A system for treating a bone, comprising:
a master fixation element including:
a shaft extending substantially along a longitudinal axis of the fixation element, wherein the shaft is threaded to threadably engage the bone; and
a head extending from and integrally formed with the shall, the head defining a plurality of fixation element openings distributed about a perimeter thereof, each of the fixation element openings extending through the head from a proximal surface thereof to a distal surface of the head, each of the fixation element openings extending through the head along an opening axis, wherein at least two of the openings are only partially enclosed by the head; and
a plurality of supplemental bone fixation elements sized and shaped for insertion through respective ones of the fixation element openings, a first one of the supplemental bone fixation elements including a threading on a head thereof adapted to lockingly mate with a corresponding thread on the one of the fixation element openings into which it is to be inserted.

20. The system of claim 19, wherein the opening axis is angled relative to the longitudinal axis so that points of intersection of the opening axes and the longitudinal axis are proximal of the head.

21. The system of claim 19, wherein the opening axis is angled relative to the longitudinal axis so that points of intersection of the opening axes and the longitudinal axis are distal of the head.

22. The system of claim 19, a surface of the head surrounding the at least two openings extending around an angle between 240° and 270°.

23. The system of claim 19, wherein the opening axis is substantially perpendicular to the longitudinal axis.

24. The system of claim 19, wherein the head further includes a locking hole extending therethrough from the proximal surface to the distal surface along a locking axis, the locking hole being adapted and configured for receiving a locking element.

25. A device for bone fixation, comprising:
a shaft extending along a longitudinal axis; and
a head permanently attached to the shaft, wherein the shaft is rotatable relative to the head about the longitudinal axis and axially locked thereto, the head defining a plurality of fixation element openings distributed about a perimeter thereof, each of the fixation element openings extending through the head from a proximal surface thereof to a distal surface of the head, each of the fixation element openings extending through the head along an opening axis, wherein at least two of the openings are partly open only partially enclosed by the head.

26. The device of claim 25, wherein the shaft is received within a central opening of the head.

27. The device of claim 25, wherein a proximal end of the shaft includes an increased diameter portion received within a corresponding recess formed in the head, the increased diameter portion preventing the shaft from being inserted distally through the head.

28. The device of claim 27, wherein the shaft includes a reduced diameter neck received in a corresponding recess formed in the head, the reduced diameter neck preventing the shaft from being withdrawn proximally through the head.

29. The device of claim 28, wherein the reduced diameter neck is threaded.

30. The device of claim 28, wherein the head further comprises an unthreaded position receiving a threaded distal portion of the shaft, engagement of the threads with a distal end of the reduced diameter neck preventing the shaft from being withdrawn proximally from the head.

* * * * *

UNITED STATES PATENT AND TRADEMARK OFFICE
CERTIFICATE OF CORRECTION

Page 1 of 1

PATENT NO. : 10,335,214 B2
APPLICATION NO. : 12/766452
DATED : July 2, 2019
INVENTOR(S) : Appenzeller et al.

It is certified that error appears in the above-identified patent and that said Letters Patent is hereby corrected as shown below:

In the Claims

Claim 19, Column 8, Line 10:
"shall, the head defining a plurality of fixation ele-" should read "shaft, the head defining a plurality of fixation ele-"

Claim 25, Column 8, Line 54:
"openings are partly open only partially enclosed the" should read "openings are only partially enclosed by the"

Signed and Sealed this
Fourteenth Day of April, 2020

Andrei Iancu
*Director of the United States Patent and Trademark Office*